United States Patent [19]

Chang et al.

[11] 4,310,516
[45] Jan. 12, 1982

[54] COSMETIC AND PHARMACEUTICAL VEHICLE THICKENED WITH SOLID EMULSIFIER

[75] Inventors: Tiang-Shing Chang, Westfield; Lucy J. Zientek, Bayonne, both of N.J.

[73] Assignee: Block Drug Company Inc., Jersey City, N.J.

[21] Appl. No.: 117,443

[22] Filed: Feb. 1, 1980

[51] Int. Cl.³ .................. A61K 33/30; A61K 31/245; A61K 47/00
[52] U.S. Cl. .................................. 424/145; 424/310; 424/358
[58] Field of Search .............. 424/145, 310, 358, 168, 424/170, 172

[56] References Cited

U.S. PATENT DOCUMENTS

| | | | |
|---|---|---|---|
| 2,493,202 | 1/1950 | Macek | 424/365 |
| 2,627,938 | 2/1953 | Frohmader | 424/358 |
| 2,628,187 | 2/1953 | Frohmader et al. | 424/358 |
| 2,792,329 | 5/1957 | Woodward | 424/114 |
| 3,829,563 | 8/1974 | Barry et al. | 424/168 X |
| 3,873,689 | 3/1975 | Frensch et al. | 424/358 X |
| 3,881,012 | 4/1975 | Mima | 424/271 |
| 4,124,720 | 11/1978 | Wenmaekers | 424/278 |
| 4,164,564 | 8/1979 | Chen | 424/358 X |

OTHER PUBLICATIONS

Merck Index (9th Ed.), 1976, p. 495, entry 3691.

*Primary Examiner*—Frank Cacciapaglia, Jr.
*Attorney, Agent, or Firm*—Ostrolenk, Faber, Gerb & Soffen

[57] ABSTRACT

An anhydrous pseudoplastic and thixotropic oleaginous vehicle is prepared by mixing at least one solid emulsifying agent having an HLB number of 12 or less with an oleaginous material and then cooling the mixture over a temperature range of at least about 15° C., said range encompassing the pour point of said agent.

5 Claims, 2 Drawing Figures

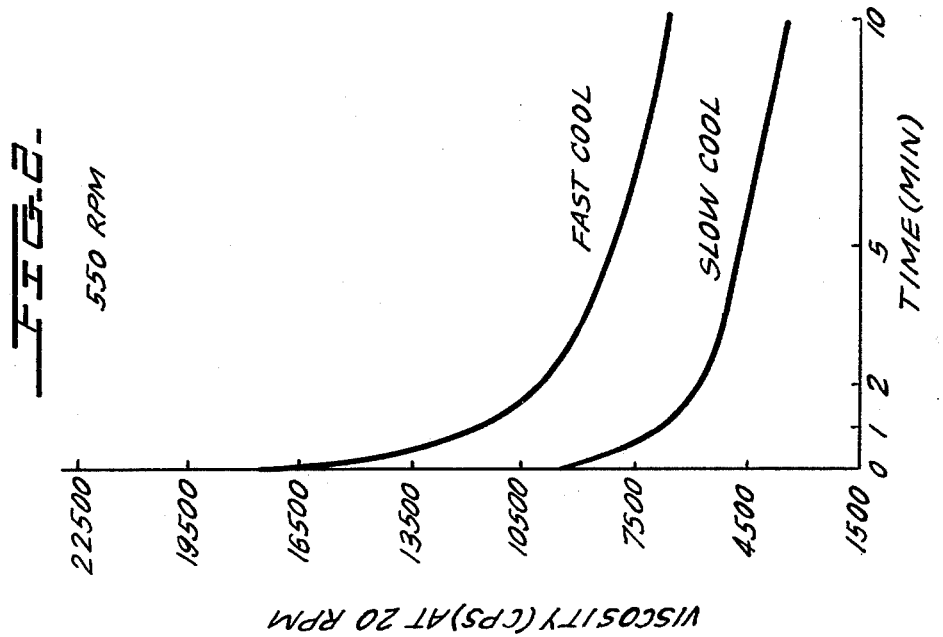
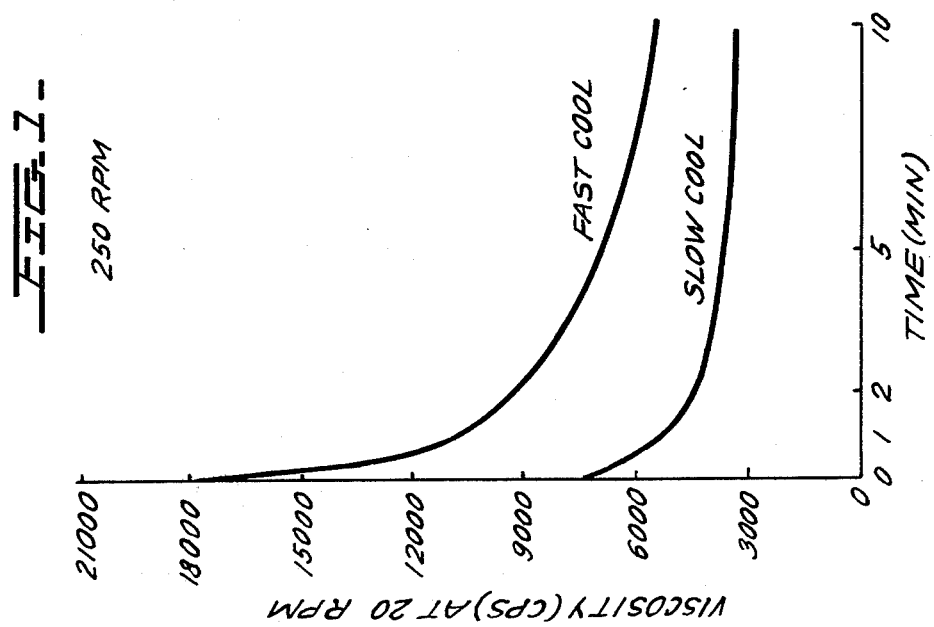

COSMETIC AND PHARMACEUTICAL VEHICLE THICKENED WITH SOLID EMULSIFIER

BACKGROUND OF THE INVENTION

Viscous compositions for use as ointments, salves, cosmetic creams and medicament carriers having petrolatum, lanolin, beeswax and the like as their base are known. Difficulties have been exhibited with such compositions in that the medicaments or other ingredients thereof tend to separate and segregate with time. In addition, their viscosity tends to change with temperature and with time, and the contained medicaments are not always readily released for absorption by the skin or other surface upon which they are used.

Mima (U.S. Pat. No. 3,881,012) teaches a pharmaceutical composition in which a liquid polyoxyethylene higher alcohol ether is mixed with an oily or fatty suppository base at elevated temperature and then cooled without stirring.

Frohmader (U.S. Pat. Nos. 2,627,938 and 2,628,187) discloses the addition of polyethylene to an oil base while stirring and heating the mixture until the polymer dissolves. The solution is then rapidly cooled without stirring through a temperature range which includes the cloud point.

An aluminum stearate gel of mineral oil is shown in Woodward (U.S. Pat. No. 2,792,329) and an oil and water emulsion of mineral oil using glycol monostearate as the emulsifier which is allowed to cool while mixing is shown in Wenmaekers (U.S. Pat. No. 4,124,720). Macek (U.S. Pat. No. 2,493,202) teaches the rapid cooling of a mixture of beeswax and peanut oil while stirring.

A new anhydrous pseudoplastic and thixotropic oleaginous vehicle has now been found which possesses hydrophobic characteristics intermediate between petroleum oil and conventional absorption bases, whose hydrophobic character can be controlled, and which can be used for the transport of water-active and/or water-sensitive ingredients.

Accordingly, it is the object of the present invention to provide a new anhydrous oleaginous vehicle whose viscosity can be reasonably controlled over a range that varies from a viscosity slightly higher than that of the unmodified base itself to that of a plastic or paste-like semi-solid; which is hydrophobic in character but miscible with water; which is non-toxic and non-irritating and as such is useful both internally as a vehicle for carrying medicaments and externally as a salve, ointment or cosmetic cream and the like. It is a further object of the invention to provide a method by which such a vehicle can be prepared. This and other objects of the invention will become apparent to those skilled in the art from the following detailed description.

SUMMARY OF THE INVENTION

This invention relates to a new anhydrous pseudoplastic and thixotropic oleaginous vehicle and the method by which it is prepared. More particularly, the anhydrous oleaginous vehicle is an anhydrous oleaginous material which is thickened by at least one solid emulsifying agent having an HLB not in excess of 12 and is prepared by mixing the oleaginous material and emulsifying agent at elevated temperature and then cooling the mixture over a temperature range of at least about 15° C., said range encompassing the melting or pour point of the agent.

DESCRIPTION OF THE INVENTION

In accordance with the present invention, an anhydrous pseudoplastic and thixotropic oleaginous vehicle is provided whose hydrophobic character is intermediate to that of a petroleum oil and a conventional absorption base and whose viscosity can be reasonably controlled over a range that varies from slightly higher than the unmodified base itself to that of a plastic or paste-like semi-solid. The vehicle is miscible with water and therefore can be used for the transport of water-active and/or water-sensitive medicaments and ingredients. In general, it is non-toxic and non-irritating and is useful both internally as a vehicle for carrying medicaments and externally as a salve, ointment or cosmetic cream and the like. The oleaginous vehicle is prepared by incorporating one or a combination of solid emulsifiers or thickening agents into a quantity of oleaginous materials such as petroleum or vegetable oil and subsequently cooling the mixture, preferably with agitation, over a temperature range of at least about 15° C. The temperature range includes the melting point or pour point of the solid emulsifier or system of emulsifiers whose HLB is 12 or less.

The viscosity and hydrophobicity of a vehicle prepared in accordance with the present invention can be controlled by the appropriate choice of the oleaginous base to be modified, the choice of the particular solid emulsifier agent or agents used and their concentration, and by the cooling rate employed to return the molten vehicle to ambient temperature, and, to a much lesser extent, by the rate of agitation employed during the cooling.

Various oleaginous materials of wide ranging viscosity can be used as the unmodified base. Such materials include the highly refined mineral oils commercially available, for example, under the trademarks Blandol and Kaydol; corn and other vegetable oils; and various fatty acids and fatty alcohols. In general, any oleaginous material heretofore used as an ointment or medicament base can be used in the present invention. Of course, combinations of such materials are also within the scope of the present invention. The use of a different oleaginous material for modification by the same solid agent while cooling at the same rate will produce products of different viscosity characteristics.

The choice of the oleaginous base to be modified and the thickening agent to be used in the practice of the present invention are important in determining the characteristics of the resulting modified vehicle. One such characteristic is the washability of the base material. Selection from a wide range of HLB values for the solid agent permits the resulting product of this invention to possess varying degrees of washability. It has been found that as the HLB values employed increase, so also does the washability of the vehicle.

Another such characteristic is the hydrophobicity of the base which is again controlled by selection of the modifying agent's HLB value. The use of an agent with a higher HLB value is desirable in a formulation where the vehicle is intended to transport a water-active ingredient such as a water-soluble gum used in a denture adhesive. Incorporation of an agent having a higher HLB value imparts a greater hydrophilicity to the formulation and can enhance the hydration of the gum. The oleaginous vehicle will still serve to protect the water-active ingredients prior to use. Therefore, the vehicle of the present invention can be preferably employed to petrolatum or similar hydrophobic preparations in such products.

The thickening agents of the present invention are characterized by being emulsifying agents, solids at ambient temperature, and having an HLB of 12 or less. The agents preferably have an HLB of about 2 to 11. Examples include glycerol fatty acid esters such as mono- and di-glycerides-stearates; sorbitan fatty acid esters such as sorbitan monolaurate and oleate; various beeswax derivatives such as Atlas G-1726 which is a polyoxyethylene 20 sorbitol beeswax derivative; various polyoxyethylene fatty ethers and polyoxyethylene fatty acid esters. The individual emulsifiers can be combined in any desired number and proportions to obtain a thickening agent which will impart to the oleaginous base a wide range of hydrophobicities, washabilities, etc. as may be desired by the formulator. In general, the thickening agent is employed in an amount from about 0.5% to about 25% by weight based on the weight of the oleaginous material and preferably about 2 to about 20% by weight.

The thickening agent is dispersed into the oleaginous base using any suitable means such as a motor driven propeller or other suitable homogenizer-mixer. The dispersion is then heated to a temperature above the melting or pour point of the solid agent preferably while being agitated. It is preferred to heat the dispersion to a temperature at least 10° above the melting or pour point and most preferably to about 15° above the melting or pour point of the solid agent. After the thickening agent has dissolved in the oleaginous base, the solution is removed from heat and cooled to a temperature below the cloud point, i.e. the point at which the solution begins to change from one that is substantially clear to one that has a translucent or cloudy appearance, at a rate that has been found to be effective in attaining the desired vehicle viscosity, employing a given concentration of the chosen emulsifier-thickening agent. The modified vehicle is agitated during cooling to assure uniformity of the base. Alternatively, the thickening agent can be dispersed in the base at the elevated temperature; or the agent can be melted prior to its addition to the unmodified base which has been preheated to an elevated temperature.

The cooling rate can vary from one which is termed a "natural cool", i.e. the solution sits at room temperature until it has cooled down to ambient, to about 30° C./min. or even greater. Preferably the cooling rate is about 0.5°-20° C. per minute. The rate of cooling has a very substantial effect on the viscosity and thixotropic and pseudoplastic properties of the modified vehicle of the present invention. Faster cooling rates will yield preparations of increasing thixotropy, viscosity and pseudoplasticity.

The agitation rate employed during cooling has also been found to have a small but measurable effect on the thickness of the resulting modified vehicle. In general, the cooling mixture is preferably agitated at a rate just sufficient to assure uniformity of the base during cooling.

Another means of controlling the product vehicle viscosity is by varying the concentration of the solid agent in the preparation. In general, the greater the proportion of the solid surface active agent, the more viscous is the resulting product. However, varying the concentration of the agent will affect the water absorption capacity, hydrophobicity and washability of the product.

The modified vehicle of the present invention exhibits numerous advantages such as those advantages implicit in its pseudoplastic and thixotropic properties. For example, the product can be more easily extruded from a tube or container and more easily spread than petrolatum based products. Therefore, the use of the vehicle in combination with such materials as dermatological medicaments can be expected to lead to less traumatization of the site of application.

Another advantage of the invention is that it can be used to enhance the performance of water-active ingredients. By appropriate selection of the solid modifying agent, the agent's HLB value and its concentration in the preparation, the resulting product can be formulated to a desired hydrophilicity and water absorption capacity. The product can then be used to enhance or impede the performance of water-active and/or water-sensitive ingredients carried by the modified base of the present invention, as desired. This capability does not exist when petrolatum and other similar unmodified or oleaginous materials are employed as vehicles for such ingredients.

A further advantage of the present invention is that it is generally non-toxic and non-irritating. These attributes readily enable the modified vehicle to be used as an internal and external vehicle for the transport of medicaments.

Additionally, the invention provides a wide range of washabilities. Its many and varied uses makes it more desirable as a vehicle than any other presently used preparations, in certain cases. For example, polyethylene is presently used to thicken mineral oil, resulting in a composition commonly referred to as Plastibase. The modified vehicle of the present invention not only thickens the oil, as does the polyethylene, but can be used to make the resulting product more washable and enhance the activity of water-active ingredients that may be incorporated with it, an advantage not enjoyed by Plastibase per se.

In order to further illustrate the present invention, various examples are given below. Unless otherwise specified, all parts and percentages in these examples, as well as throughout the balance of this specification and claims are by weight and all temperatures in degrees Centigrade.

EXAMPLES 1-6

Six compositions were prepared in the same manner except for the cooling rates and agitation rates. Each composition was prepared by dispersing 15 grams of glyceryl stearate (Atmul 84S), a solid surfactant having an HLB of 2.8 and a pour point of 58° C., with mechanical agitation in 285 grams of mineral oil (Kaydol) at 70° C. After dissolution of the solid additive, the compositions were cooled from a temperature approximately 15° C. above the cloud point (55° C.) to a temperature 15° C. below the cloud point.

Three of the compositions thus prepared were cooled at a rate of 1.5° C./min (slow cool). Two of these were agitated during cooling with a three-bladed, 2-inch diameter propeller attached to a Lightnin Mixer LM rotating at either 250 or 550 rpm, respectively. The third ("no agitation") was only mixed periodically with a spatula in order to aid homogeneity.

The other three compositions were cooled at a rate of 13° C./min. (fast cool) and mixed in the same manner as described in the preceding paragraph.

The effects of the cooling and agitation rate from the composition viscosity are shown in Table 1.

TABLE 1

Base Viscosities (cps) @ 20 rpm, 25° C., Measured with Brookfield Viscometer

| Agitation Rate | Cooling Rate | |
|---|---|---|
| | 13° C./minute | 1.5° C./minute |
| 550 RPM | 22,700 | 10,100 |
| 250 RPM | 18,200 | 7,950 |
| No Agitation | 17,600 | 5,350 |

FIG. 1 illustrates the viscosity/time relationship at the 250 rpm rate of agitation and FIG. 2 shows the same relationship at the 550 rpm rate of agitation.

EXAMPLES 7–10

The following three compositions were prepared by dissolving the solid emulsifier in the oleaginous base at a temperature about 15° C. above the pour point of the solid emulsifier. The molten mixtures were then cooled at a rate of 3° C./min. while mixing with a spatula periodically to assume uniformity of the base. The compositions and their resulting viscosities are set forth in Table 2.

| Preparation | | Viscosity (25° C. RVT Spindle 5 RPM Brookfield) |
|---|---|---|
| EXAMPLE 7 | | |
| Brij 72 (Polyoxethylene 2 cetyl ether; HLB = 4.9; pour point 43° C.) | 20.0% | 386,000 cps |
| Kaydol (Mineral oil) | 80.0% | |
| EXAMPLE 8 | | |
| Atmul 84S (Glyceryl stearate; HLB = 2.8; pour point 58° C. | 20.0% | 1,300,000 cps |
| Isostearic acid | 80.0% | |
| EXAMPLE 9 | | |
| Atlas G-1726 (Polyoxyethylene 20 Soribtan Beeswax; HLB = 5; pour point 63° C.) | 15.0% | 74,800 cps |
| Isocetyl alcohol | 85.0% | |

EXAMPLES 10–13

The following compositions were prepared by dissolving the solid emulsifier in the oleaginous base at a temperature about 15° C. above the pour point of the solid emulsifying agent. The molten mixture was then cooled at a rate of 10° C. per minute while mixing with a three-bladed, 2-inch diameter propeller attached to a Lightnin Mixer, rotated at 250 rpm, over a temperature range of 30° C. that included the cloud point of the solution. The compositions and the resulting viscosities are given in Table 3.

| Preparation | | Viscosity (25° C., RVT Spindle, 5 RPM Brookfield) |
|---|---|---|
| EXAMPLE 10 | | |
| Glyceryl stearate (Atmul 84S, HLB 2.8; pour point 58° C.) | 2.0% | 1,900 cps |
| Kaydol (Mineral Oil) | 98.0% | |
| EXAMPLE 11 | | |
| Glyceryl stearate (Atmul 84S, HLB 2.8; pour point 58° C.) | 3.0% | 3,760 cps |

| Preparation | | Viscosity (25° C., RVT Spindle, 5 RPM Brookfield) |
|---|---|---|
| Kaydol (Mineral Oil) | | 97.0% |
| EXAMPLE 12 | | |
| Sorbitan palmitate (Arlacel 40, HLB = 6.7 pour point 48° C.) | 2.0% | 980 cps |
| Kaydol (Mineral Oil) | 98.0% | |
| EXAMPLE 13 | | |
| Sorbitan palmitate (Arlacel 40, HLB = 6.7 pour point 48° C.) | 3.0% | 1,280 cps |
| Kaydol (Mineral Oil) | 97.0% | |

EXAMPLE 14

The following composition was prepared by dissolving the solid emulsifier in a blended oleaginous base at a temperature 15° C. above the pour point of the solid emulsifying agent. The molten mixture was then cooled at a rate of 9° C. per minute while mixing with three-bladed 2-inch diameter propeller rotated at 250 RPM, over a temperature range of 30° C. that included the cloud point of the solution. The composition and its resulting viscosity are given below.

| Preparation | | Viscosity (25° C., 20 RPM, Brookfield) |
|---|---|---|
| Atlas G1726 (Polyoxyethylene 20 Sorbitan Beeswax; HLB = 5, pour point 63° C.) | 10% | 150 cps |
| Isocetyl alcohol | 45% | |
| Blandol (Mineral Oil) | 45% | |

EXAMPLE 15

The following composition was prepared by dissolving two solid emulsifiers in an oleaginous base at 70° C. The molten mixture was then cooled at a rate of 4° C. per minute while mixing with three-bladed 2-inch diameter propeller attached to a Lightnin Mixer, rotated at 250 RPM, over a temperature range of 30° C. that included the cloud point of the solution. The composition and the resulting viscosity is given below.

| Preparation | | Viscosity (25° C., 20 RPM, Brookfield) |
|---|---|---|
| Brij 72 (Polyoxyethylene 2 cetyl ether, HLB = 49; pour point 43° C.) | 8.75% | 5,100 cps |
| Arlacel 165 (Glycerol monostearate and Polyoxyethylene stearate blend; HLB = 11.0; pour point 54° C.) | 16.25% | |
| Kaydol (Mineral Oil) | 75.00% | |

EXAMPLES 16–17

The invention may be employed to prepare a vehicle for use in the following ointment formulations:

| Example 16 | |
|---|---|
| Composition prepared according to Example 7 from ca 89% Kaydol (Mineral Oil) and ca 11% Atmul 84S (glyceryl stearate) | 92.9% |
| Benzocaine | 7.0% |
| Menthol | 0.1% |
| Preservative and flavor | Q.S. |
| Example 17 | |

-continued

| Composition prepared according to Example 7 from ca 87% Blandol (Mineral Oil) and ca 13% Atmul 124 (Mono-and Di-glyceride) | 80% |
|---|---|
| Zinc oxide | 20% |
| Preservative and flavor | Q.S. |

EXAMPLE 18

The invention may be employed to prepare a vehicle for use in water active or water sensitive formulations, such as denture adhesives, as follows:

| Composition prepared according to Example 7 from ca 59.5% Blandol (Mineral Oil), ca 39% Petrolatum USP and ca 1.5% Atmul 84S | 65% |
|---|---|
| Polyox WSR-301 (Polyethylene oxide) | 35% |
| Preservative, coloring and flavor | Q.S. |

Various changes and modifications can be made in the process and products of this invention without departing from the spirit and scope thereof. For example, since an object of the invention is to provide a vehicle for the transport of internal and external medicaments, the selection of the solid agent(s) and oleaginous base will be made considering the toxicity and irritation potentials of the materials unless it is the intent to develop a vehicle for use in other than physiological systems. Also, the compatibility of the oleaginous base and solid surfactant with the material intended to be carried by the modified vehicle will be considered. The judicious selection of ingredients can not only facilitate transport but can also enhance the performance of the active ingredient(s). Compatible materials can be combined in any proportions to yield an oleaginous base of desired hydrophobicity, viscosity, etc. Accordingly, the foregoing embodiments were intended to further illustrate the invention only and were not intended to limit it.

We claim:

1. A method of preparing an anhydrous pseudoplastic and thixotropic oleaginous vehicle which comprises cooling at a rate of about 0.5° to 30° C./min. a mixture of at least one solid at ambient temperature emulsifying agent whose HLB is not in excess of 12 with at least one oleaginous material selected from the group consisting of mineral oil, fatty acid, and fatty alcohol, with agitation, over a temperature range of at least about 15° C., said range encompassing the pour point of said agent.

2. The method of claim 1 wherein said mixture is cooled at a rate about 0.5° C./min. to 20° C./min.

3. The method of claim 2 wherein said solid emulsifying agent comprises about 0.5–25% by weight of said mixture.

4. The method of claim 3 wherein said oleaginous material is mineral oil.

5. The method of claim 4 wherein said solid agent is about 2–20% of said mixture.

* * * * *